United States Patent [19]

Lomoelder et al.

[11] Patent Number: 5,449,827

[45] Date of Patent: Sep. 12, 1995

[54] AZOMETHINE, A PROCESS FOR THE PREPARATION THEREOF AND ALSO ITS USE

[75] Inventors: Rainer Lomoelder, Muenster; Wilfried Paulen, Recklinghausen; Felix Schmitt, Herten; Elmar Wolf, Recklinghausen, all of Germany

[73] Assignee: Huels Aktiengesellschaft, Marl, Germany

[21] Appl. No.: 206,860

[22] Filed: Mar. 7, 1994

[30] Foreign Application Priority Data

Apr. 10, 1993 [DE] Germany ............... 43 11 901.8

[51] Int. Cl.6 ............ C07C 251/04; C07C 249/02; C07C 229/00; C07D 251/30
[52] U.S. Cl. .................. 564/248; 564/271; 564/272; 564/276; 564/278; 521/166; 528/61
[58] Field of Search ........... 564/248, 272, 276, 278, 564/271

[56] References Cited

U.S. PATENT DOCUMENTS

| | | | |
|---|---|---|---|
| 714,931 | 12/1902 | Merling | 564/248 X |
| 1,864,067 | 6/1932 | Howland | 564/276 X |
| 2,027,902 | 1/1935 | Dahlen | 564/276 X |
| 2,155,356 | 4/1939 | Britton et al. | 564/276 X |
| 2,220,065 | 11/1940 | Clarkson | 564/276 |
| 2,424,061 | 7/1946 | Shonle et al. | 564/248 X |
| 3,352,913 | 11/1967 | Schmitt et al. | 564/248 |
| 3,481,981 | 12/1969 | Moffett | 564/276 |
| 3,743,667 | 7/1973 | Wagner et al. | 564/248 X |
| 3,835,191 | 9/1974 | Wagner et al. | 564/248 X |
| 4,108,842 | 8/1978 | Konig et al. | 528/61 |
| 4,224,417 | 9/1980 | Hajek et al. | 521/166 |
| 4,783,468 | 11/1988 | Kristinsson | 514/275 |

FOREIGN PATENT DOCUMENTS

| | | | |
|---|---|---|---|
| 2362171 | 8/1976 | France | 564/248 |
| 2328006 | 5/1977 | France | 564/248 |
| 2356213 | 5/1975 | Germany | 564/248 |
| WO8200142 | 1/1982 | WIPO | 564/248 |
| WO8504873 | 11/1985 | WIPO | 564/248 |

OTHER PUBLICATIONS

Klicnar et al, Collection Czech. Chem. Commun., vol. 33, pp. 994–998 (1968).
Chem. Ber. 101, 1244–1249 (1968) Eckhardt Allenstein & Rainer Fuchs.
Chem. Ber 101, 1232–1243 (1968) Eckhard Allenstein & Rainer Fuchs.
95774w, Chem. Abst, vol. 68 Eckhard et al (1974).
104544a, Chem. Abst, vol. 68 Eckhard et al (1974).
W. J. Middleton & V. A. Englehardt, vol. 80 pp. 2788–2795 J. Am. Chem. Soc. (1958).

*Primary Examiner*—Floyd D. Higel
*Attorney, Agent, or Firm*—Oblon, Spivak, McClelland, Maier & Neustadt

[57] ABSTRACT

The invention relates to an azomethine of the following composition:

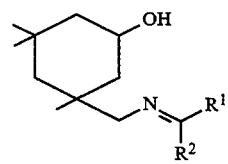

in which
  $R^1$ is H or a branched or unbranched $C_{1-14}$-alkyl radical, and
  $R^2$ is a branched or unbranched $C_{1-14}$-alkyl radical, an $C_{1-14}$ alkyl-substituted phenyl radical or a $C_1$–$C_8$-(cyclo)-alkyl radical.

It further relates to a process for preparing an azomethine, in which

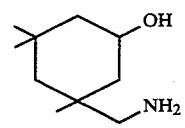

(Abstract continued on next page.)

is reacted with the corresponding carbonyl compounds
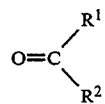
The invention also relates to the use of the azomethines for the preparation of certain polyazomethines (poly-Schiff bases), where the azomethines are reacted with diisocyanates or their adducts with polyols or their trimers, and to polyazomethine compounds.
2 Claims, No Drawings

AZOMETHINE, A PROCESS FOR THE PREPARATION THEREOF AND ALSO ITS USE

This application claims the benefit of priority under 35 U.S.C. 119 to DE P43 11 901.8 filed in Germany Apr. 10, 1993, the entire contents of which are hereby incorporated by reference.

BACKGROUND OF THE INVENTION

1. Field of the Invention

The present invention relates to a new azomethine, a process for the preparation thereof and also its use.

2. Discussion of the Background

Azomethines, better known under the name Schiff bases, are generally prepared by condensation of a primary amine and a carbonyl compound:

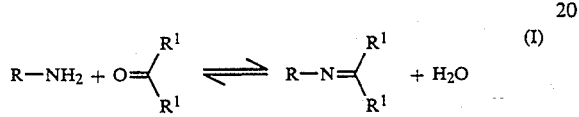

If the $H_2O$ is removed from the equilibrium, the azomethine can be obtained in almost quantitative yield. However, primary 2-hydroxyamines react with carbonyl compounds to give a mixture of Schiff bases and oxazolidines (A. Paquin, B. 82, 316 (1949)), the two reaction products being in equilibrium with each other:

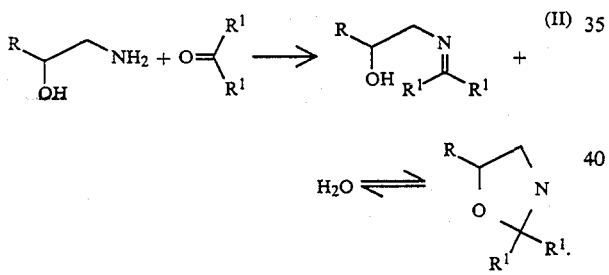

3- or 4-hydroxyamines react analogously with carbonyl compounds to give 6- or 7-membered ring systems.

Starting from a 4-hydroxyamine and a carbonyl compound, aldehyde or ketone, the Schiff base according to equation I can only be prepared as a mixture with a 7-membered N,O-heterocycle. A Schiff base from a 4-hydroxyamine would be of great interest for the preparation of poly(Schiff base)s, since hydrolysis would then give a simple route to polyamines which can be obtained only with great difficulty, if at all, in other ways.

SUMMARY OF THE INVENTION

It was therefore an object of the invention to seek 4-hydroxyamines which would react with carbonyl compounds in a simple manner and without byproduct formation to give azomethines whose OH groups are in the δ-position to the N of the azomethine group.

This object is achieved by use of a hydroxyamine of the formula:

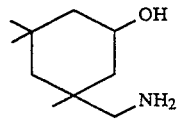

3-aminomethyl-3,5,5-trimethyl cyclohexanol (hereinafter IPAA).

Accordingly one object of the present invention is to provide an azomethine (Schiff base) of the composition:

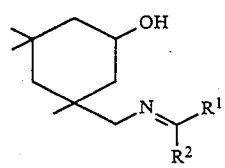

wherein
$R^1$ is H or a branched or unbranched $C_{1-14}$-alkyl radical, and $R^2$ is a branched or unbranched $C_{1-14}$-alkyl radical, an $C_{1-14}$ alkyl-substituted phenyl radical or a $C_1-C_8$-cycloalkyl radical.

The azomethine compound of the invention is a low-viscosity product having a Gardner colour number <1 and an amine content of from 2 to 5 mmol/g and an OH number (mg KOH/g) of from 100 to 280.

Another embodiment of the present invention is to provide a process for preparing an azomethine

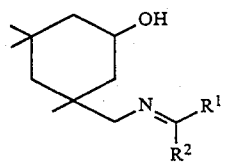

wherein
$R^1$ is H or a branched or unbranched $C_{1-14}$-alkyl radical, and $R^2$ is a branched or unbranched $C_{1-14}$-alkyl radical, an $C_{1-14}$ alkyl-substituted phenyl radical or a $C_1-C_8$-cycloalkyl radical, comprising reacting an amino alcohol:

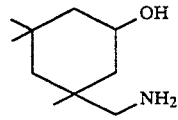

with a carbonyl compound of the formula:

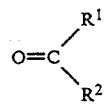

wherein $R^1$ is H or a branched or unbranched $C_{1-14}$-alkyl radical, and $R^2$ is a branched or unbranched $C_{1-14}$-alkyl radical, an $C_{1-14}$ alkyl-substituted phenyl radical or a $C_1-C_8$- cycloalkyl radical; in a molar ratio of 1:1–1.3 at temperatures from 60° to 140° C.

Another embodiment of the present invention is to provide a novel polyazomethine:

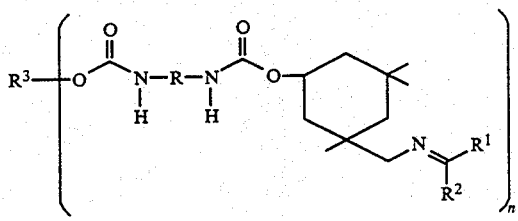

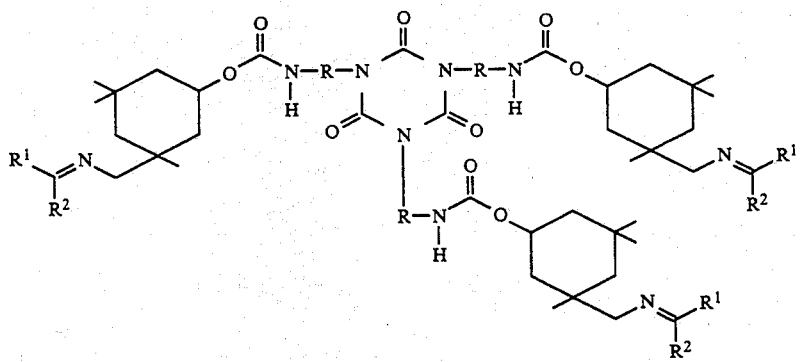

in which 1≦n≦6, wherein
R is the hydrocarbon radical of a (cyclo)aliphatic, araliphatic or aromatic diisocyanate having 6–20 carbon atoms or trimers thereof, and when 2≦n≦6 $R^3$ is an n-valent organic radical as is obtained by removal of n OH groups from a polyhydroxyl compound which may optionally contain ether oxygen atoms or from a hydroxyl-containing polyester compound having an average molecular weight between 40 and 5,000, or
when n=1, $R^3$ is

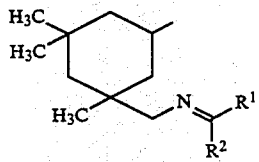

$R^1$ is H or a branched or unbranched $C_{1-14}$-alkyl radical, and
$R^2$ is a branched or unbranched $C_{1-14}$-alkyl radical, an $C_{1-14}$ alkyl-substituted phenyl radical or a $C_1$–$C_8$-cycloalkyl radical.

Another embodiment of the present invention is to provide a method for preparing a polyazomethine by reaction of a diisocyanate, or their adducts of the following composition:

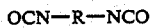

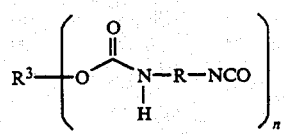

with the azomethines of the invention having the general composition:

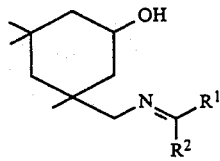

in which R, $R^1$, $R^2$ and $R^3$ have the meanings given above, in an NCO:OH equivalence ratio of 1:1.

The objects of the present invention are provided for by the discovery that, upon reaction with a carbonyl compound, 3-amino-3,5,5-trimethyl cyclohexanol forms a Schiff base, and not the cyclic 7-membered ring system.

DETAILED DESCRIPTION OF THE PREFERRED EMBODIMENTS

Preparation of Azomethine:
The preparation can be carried out either in solution or without solvent.

When the reaction is carried out in solution, toluene or xylene is preferred as (inert) solvent. The azomethine formation can be accelerated by addition of 0.01–0.1% by weight of acid such as $H_3PO_4$. This is advantageous when sluggishly reacting components are used, as is the case with sterically hindered amines and ketones. IPAA and toluene are mixed at room temperature and admixed with an equimolar amount of the carbonyl compound. The concentration of toluene is from about 50 to 80% by weight. The solution is then slowly heated to reflux and heated further with a water separator attached until the calculated amount of H₂O has been distilled off. The toluene is then distilled off in vacuo. The concentration of the Schiff base so prepared is ≧99% (% by area in the gas chromatogram). In general, this purity is sufficient for further reaction of the Schiff base with NCO prepolymers to form poly-Schiff bases.

In the preparation without solvent, equimolar amounts of IPAA and the carbonyl component are mixed at room temperature and slowly heated to reflux and heated further until the calculated amount of H₂O has been distilled off. It has proven advantageous to add the carbonyl component in an excess of from 10 to 30 wt. %. After the distillative separation of the water of reaction and the excess carbonyl component, vacuum is applied for a short time. The product of the process, thus prepared, according to the invention, has a purity of ≧99% and generally needs no further purification.

In principle as the carbonyl compound, all aldehydes and ketones are suitable for blocking the NH₂ function, provided that the carbonyl compound is capable of forming an azomethine group with the primary amine. Blocking agents which have proved to be particularly suitable are for example, from the aldehydes: acetaldehyde, propionaldehyde, n-butyraldehyde and i-butyraldehyde, and from the ketones: methyl ethyl ketone, methyl n-propyl ketone, diethyl ketone, methyl isobutyl ketone and diisobutyl ketone.

The azomethine compound of the present invention is useful in the preparation polyamine compounds.

Preparation of Polyazomethine:

The present invention also provides for a method for the preparation of a polyazomethine (poly-Schiff base) using an azomethine of the invention having the following composition:

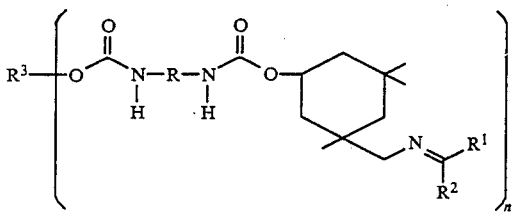

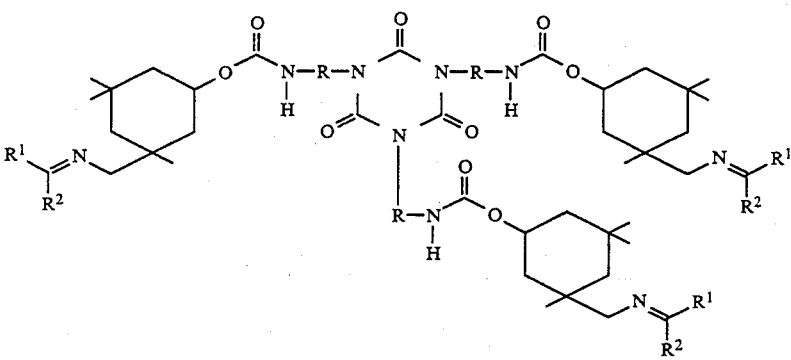

in which 1≦n≦6, wherein
R is the hydrocarbon radical of a (cyclo)aliphatic, araliphatic or aromatic diisocyanate having 6–20 carbon atoms or trimers thereof, and when
2≦n≦6 R³ is an n-valent organic radical as is obtained by removal of n OH groups from a polyhydroxyl compound which may optionally contain ether oxygen atoms or from a hydroxyl-containing polyester compound having an average molecular weight between 40 and 5,000, or when n=1, R³ is

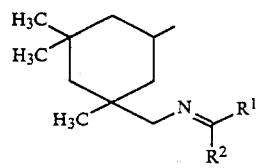

R¹ is H or a branched or unbranched $C_{1-14}$-alkyl radical, and
R² is a branched or unbranched $C_{1-14}$-alkyl radical, an $C_{1-14}$ alkyl-substituted phenyl radical or a $C_1$–$C_8$-cycloalkyl radical.

The preparation of the polyazomethines of the invention is carried out by reaction of a diisocyanate, or their adducts of the following composition:

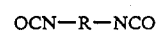

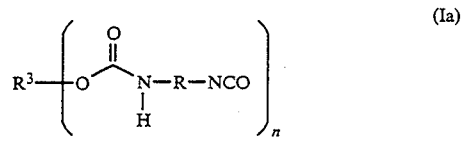

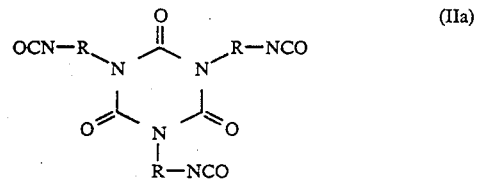

with the azomethines of the invention having the general composition:

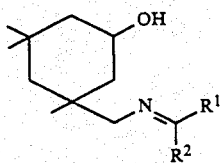

in which R, $R^1$, $R^2$ and $R^3$ have the meanings given above, in an NCO:OH equivalence ratio of 1:1.

Depending on the state of aggregation of the diisocyanate or NCO prepolymer used, the reaction is carried out without solvent or in aprotic solvents at temperatures of from 20° to 80° C.

In the case of low-viscosity NCO prepolymers, solvent can be omitted; in the case highly viscous and solid NCO prepolymers, however, solvent must be used. Possible solvents are, in principle, all those which contain no functional groups which react with NCO groups. Solvents which have proven particularly suitable ketones, such as acetone, methyl ethyl ketone, and aromatic hydrocarbons, such as toluene.

Preparation of isocyanate:

The isocyanate prepolymers (Ia; IIa) used for the process of the invention are prepared according to methods known per se by reaction of polyhydroxy compounds with diisocyanates or by trimerization of diisocyanates.

Suitable polyhydroxy compounds are polyols having a molecular weight of from 60 to 600, such as ethylene glycol, hexanediol, di- and triethyleneglycol, neopentylglycol, trimethylolpropane, octadecanediol and $C_{36}$-diol. Preference is given to polyether polyols having a molecular weight of 200–5,000, and having 2–5, preferably 2–3, hydroxyl groups. Possible OH group-containing polyethers according to the invention are those of a type known per se and are prepared, for example, by polymerization of epoxides, such as ethylene oxide, propylene oxide, tetrahydrofuran or styrene oxide, with themselves, for example in the presence of Lewis acids such as $BF_3$, or by addition of these epoxides either in a mixture or successively to initiator components having reactive hydrogen atoms, such as $H_2O$, alcohols and amines. Furthermore, OH group-containing polybutadienes are used for the isocyanate prepolymers, as are hydroxyl-containing polyesters and polyketones.

Possible starting components for the preparation of the isocyanate prepolymers (Ia; IIa) required for the process of the invention are (cyclo)aliphatic, araliphatic or aromatic diisocyanates, as are described, for example, by W. Siefken in Justus Liebigs Annalen der Chemie, Vol. 562, p. 75–136, for example 1,6-hexamethylene diisocyanate, 2-methylpentamethylene 1,5-diisocyanate, 1,12-dodecane diisocyanate, isophorone diisocyanate, tetramethylxylylene diisocyanate, 2,4- and 2,6-tolylene diisocyanate and diphenylmethane 2,4'- and/or 4,4'-diisocyanate.

The isocyanate prepolymers are generally prepared by reacting 1 OH-equivalent of the polyol together with 2 NCO-equivalents of the diisocyanate in a known manner. The isocyanate prepolymers so prepared still contain, depending on molecular weight, about 2–8 wt. % of free diisocyanate. In some cases it has proven advantageous to use isocyanate prepolymers having a diisocyanate constant <0.5 wt. % for the process of the invention. Such "low monomer" isocyanate prepolymers are prepared by, in a first stage, reacting the diisocyanate in a large excess with the polyol and, in a second stage, removing the unreacted diisocyanate from the reaction product by thin-film distillation. The isocyanate prepolymers prepared in this way contain, independently of their molecular weight, <0.5 wt. % of diisocyanate.

The isocyanate prepolymers IIa used for the process of the invention are prepared in a known way by trimerization of the diisocyanates already listed for the preparation of the isocyanate prepolymers Ia. Trimerization catalysts which have proven advantageous are those described in DE-C 26 44 684 and DE-C 29 16 201.

According to the polyamine of formula Ia, when $2 \leq n \leq 6$, the group $R^3$ is an n-valent organic radical. A suitable example is the organic radical formed by removing n hydroxy groups from a polyhydroxy compound which optionally contains ether oxygen atoms. Suitable polyhydroxy compounds include ethylene glycol, glycerol, hexanediol, di- and triethylene glycol, neopentylglycol, trimethylolpropane, octadecanediol, pentaerythritol, sorbitol, mannitol, maltitol and glycosides.

The reaction components used according to the processes of the invention for the diisocyanates and the isocyanates prepolymers (Ia, IIa) are the azomethines (Schiff bases) of the invention.

The polyazomethine of the invention are outstandingly suitable for the simple preparation of polyamines which cannot be prepared, or can be prepared only with difficulty, in other ways. The polyamines are prepared by hydrolysis of the polyazomethine as follows:

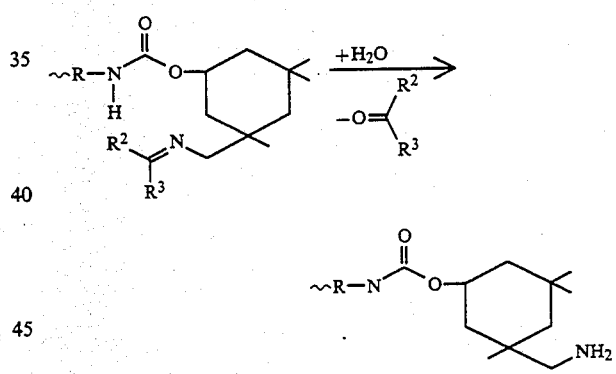

The carbonyl compounds are split off in a manner such that the polyazomethine, if appropriate in the presence of 0.1–0.5% of emulsifiers, is heated with excess $H_2O$ (2–3 times the molar amount of the polyazomethine) while stirring intensively, $H_2O$, the carbonyl compound liberated and, if appropriate, the solvent being distilled off simultaneously under atmospheric pressure.

After removing the last residues of $H_2O$, the polyamine is further heated in vacuo at 100°–140° C. for about 2–4 hours. The polyamines thus prepared no longer contain azomethine groups; rather exclusively primary $NH_2$ groups are present. The $H_2O$ content is 0.1–0.6% wt.

Having generally described this invention, a further understanding can be obtained by reference to certain specific examples which are provided herein for purposes of illustration only and are not intended to be limiting unless otherwise specified.

Experimental Part

A. Preparation of the azomethine (mono (Schiff base)s) of the invention

EXAMPLE 1

342 parts by weight of IPAA were mixed with 260 parts by eight of methyl isobutyl ketone (MIBK) at room temperature and slowly heated to reflux with a water separator attached and subsequently heated further at this temperature (about 130° C.) until 36 parts by weight of $H_2O$ and the excess MIBK had been distilled off. The reaction product was then distilled further in a water-pump vacuum (2% distillate). The reaction product so prepared could be used without further purification for the preparation of poly-Schiff bases. The amine content of the reaction product was 3.89 mmol $NH_2/g$; its viscosity (23° C.) was 2610 mPa•s.

EXAMPLE 2

342 parts by weight of IPAA were reacted analogously to Example 1 with 180 parts by weight of methyl ethyl ketone.

The reaction product had a basic amine content of 4.3 mmol $NH_2/g$ and a viscosity at 3° C. of 2130 mPa•s.

EXAMPLE 3

342 parts by weight of IPAA were reacted analogously to Example 1 with 300 parts by weight of diisobutyl ketone.

The reaction product had a basic amine content of 3.25 mmol $NH_2/g$ and a viscosity of 23° C. of 15300 mPa•s.

EXAMPLE 4

342 parts by weight of IPAA and 180 parts by weight of isobutyraldehyde were mixed with 500 parts by weight of toluene at room temperature and slowly reacted to reflux with a water separator attached and maintained at this temperature until 36 parts by weight of $H_2O$ had been distilled off. The major part of the toluene (and the unreacted isobutyraldehyde) was distilled off at atmospheric pressure. To remove the remaining toluene, the reaction product was heated further for a short time in a water-pump vacuum.

The azomethine so prepared had a purity of >99% (% by area in the gas chromatogram), a basic amine content of 4.3 mmol $NH_2/g$ and a viscosity of at 23° C. of 1320 mPa•s.

EXAMPLE 5

342 parts by weight of IPAA and 285 parts by weight of 3,5,5-trimethylcyclohexanone were reacted analogously to Example 4 with 500 parts by weight of toluene.

The reaction product had a basic amine content of 3.39 mmol $NH_2/g$ and a viscosity of 31600 mPa•s.

B. Preparation of the polyaxomethines (poly-Schiff bases) of the invention

EXAMPLE 1

253 parts by weight of the Schiff base from Example A.1 and 560 parts by weight of an NCO prepolymer which had been prepared by a known method from 444 parts by weight of IPDI and 650 parts by weight of a polytetrahydrofuran-diol having an average molecular weight of 650 were heated at 50° C. until NCO could no longer be detected (about 20 hours).

The reaction product had a basic amine content of 1.2 mmol $NH_2/g$ and a viscosity 23° C. of $750 \times 10^3$ mPa•s.

EXAMPLE 2

225 parts by weight of the Schiff base from Example A.2 and 737 parts by weight of the NCO prepolymer which had been prepared by a known method from 444 parts by weight of IPDI and 1000 parts by weight of a polytetrahydrofurandiol having an average molecular weight of 1000 were reacted analogously to Example 1.

The reaction product had a basic amine content of 1.03 mmol $NH_2/g$ and a viscosity at 23° C. of $810 \times 10^3$ mPa•s.

EXAMPLE 3

295 parts by weight of the Schiff base from Example A.3 and 1,313 parts by weight of an isocyanate polymer which had been prepared by a known method from 444 parts by weight of IPDI and 2000 parts by weight of a bifunctional polypropylene glycol with an average molecular weight of 2000, were reacted analogously to Example 1.

The reaction product had a basic amine content of 0.6 mmol $NH_2/g$ and a viscosity at 23° C. of $67 \times 10^3$ mPa•s.

EXAMPLE 4

244 parts by weight IPDI with 17.2% NCO (VESTANAT T 1890, a commercial product of Huels AG) was dissolved in 300 parts by weight of the Schiff base A1 until the NCO content was <0.1%. Then the acetone was distilled off under normal pressure. For complete removal of the acetone, the reaction product was further heated under water aspirator vacuum at 120° C.

The reaction product had a basic amine content of 1.2 mmol $NH_2/g$ and a melting range of 165°–169° C.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. An azomethine of the formula:

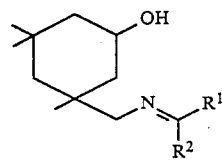

wherein
R[1] is H or a branched or unbranched $C_{1-14}$-alkyl radical, and
R[2] is a branched or unbranched $C_{1-14}$-alkyl radical, an $C_{1-14}$ alkyl-substituted phenyl radical or a $C_1$–$C_8$-cycloalkyl radical.

2. A process for preparing an azomethine of the formula:

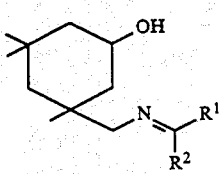

wherein

R$^1$ is H or a branched or unbranched C$_{1-14}$-alkyl radical, and

R$^2$ is a branched or unbranched C$_{1-14}$-alkyl radical, an C$_{1-14}$ alkyl-substituted phenyl radical or a C$_1$–C$_8$-cycloalkyl radical, comprising:

reacting an amino alcohol

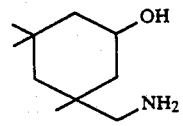

with a carbonyl compound of the formula:

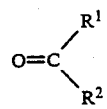

wherein R$^1$ is H or a branched or unbranched C$_{1-14}$-alkyl radical, and

R$^2$ is a branched or unbranched C$_{1-14}$-alkyl radical, an C$_{1-14}$ alkyl-substituted phenyl radical or a C$_1$–C$_8$-cycloalkyl radical, in a molar ratio of 1:1–1.3 at temperatures from 60° to 140° C.

* * * * *